(12) United States Patent
Oshmyansky

(10) Patent No.: US 9,255,423 B2
(45) Date of Patent: Feb. 9, 2016

(54) DEVICE TO PROMOTE HAND SANITIZATION

(71) Applicant: Altitude Medical, Inc., Concord, OH (US)

(72) Inventor: Alexander Roman Oshmyansky, Baltimore, MD (US)

(73) Assignee: Altitude Medical, Inc., Concord, OH (US)

( * ) Notice: Subject to any disclaimer, the term of this patent is extended or adjusted under 35 U.S.C. 154(b) by 0 days.

(21) Appl. No.: 14/455,144

(22) Filed: Aug. 8, 2014

(65) Prior Publication Data

US 2014/0346194 A1 Nov. 27, 2014

Related U.S. Application Data

(63) Continuation of application No. 12/070,429, filed on Feb. 19, 2008, now abandoned.

(60) Provisional application No. 60/933,118, filed on Jun. 5, 2007.

(51) Int. Cl.
*E05B 1/00* (2006.01)
*A61L 2/18* (2006.01)

(52) U.S. Cl.
CPC ............. *E05B 1/0069* (2013.01); *A61L 2/18* (2013.01); *Y10T 292/57* (2015.04)

(58) Field of Classification Search
CPC ........ E05B 1/0069; A61L 2/18; Y10T 292/57
USPC .................................................. 422/28, 292
See application file for complete search history.

(56) References Cited

U.S. PATENT DOCUMENTS

| 2,044,904 | A | | 12/1935 | Max |
| 3,967,478 | A | | 7/1976 | Guinn |
| 4,046,508 | A | | 9/1977 | McDonald |
| 4,402,432 | A | * | 9/1983 | Corsette ..................... 222/321.2 |
| 4,710,634 | A | | 12/1987 | Brookes |
| 4,896,144 | A | | 1/1990 | Bogstad |
| 4,997,139 | A | | 3/1991 | Menard |
| 5,454,409 | A | | 10/1995 | McAffer et al. |
| 5,808,553 | A | | 9/1998 | Cunningham |
| 6,029,557 | A | | 2/2000 | Sulm et al. |

(Continued)

FOREIGN PATENT DOCUMENTS

| CA | 2296152 A1 | 6/2000 |
| DE | 19857268 A1 | 6/2000 |

(Continued)

OTHER PUBLICATIONS

PCT Search Report and Written Opinion, PCT/US2008/006505, 10 page, Date of Mailing Nov. 12, 2008.

(Continued)

*Primary Examiner* — Regina M Yoo
(74) *Attorney, Agent, or Firm* — Moser Taboada

(57) ABSTRACT

Embodiments of the invention relate to a device to promote hand sanitization, such as a device that includes an assembly used to move a door coupled to a sanitizing agent dispenser such that the dispenser releases sanitizing agent upon manipulation of the assembly to move the door onto the hand of a user and may include a latch that is coupled to the door for latching the door.

14 Claims, 9 Drawing Sheets

(56) References Cited

U.S. PATENT DOCUMENTS

| | | | |
|---|---|---|---|
| 6,029,600 | A | 2/2000 | Davis |
| 6,211,788 | B1 | 4/2001 | Lynn et al. |
| 6,289,557 | B1 | 9/2001 | Manson et al. |
| 6,577,240 | B2 | 6/2003 | Armstrong |
| 6,645,435 | B2 | 11/2003 | Dawson et al. |
| 6,874,697 | B2 | 4/2005 | Callueng |
| 6,997,394 | B1* | 2/2006 | Washington .............. 239/274 |
| 7,080,427 | B1 | 7/2006 | Campopiano et al. |
| 7,320,418 | B2 | 1/2008 | Sassoon |
| 7,338,646 | B2 | 3/2008 | Gilbert |
| 2002/0127139 | A1* | 9/2002 | Lidahl et al. ............... 422/28 |
| 2004/0223894 | A1 | 11/2004 | Gilbert |
| 2004/0237255 | A1 | 12/2004 | Lin et al. |
| 2005/0173459 | A1* | 8/2005 | Buxmann ............... 222/321.6 |
| 2006/0038417 | A1* | 2/2006 | Pudney ............... E05B 13/002 292/336.3 |
| 2006/0153733 | A1 | 7/2006 | Sassoon |
| 2006/0245818 | A1 | 11/2006 | Stropkay et al. |
| 2007/0207073 | A1* | 9/2007 | Drucker ............... A61L 2/10 422/292 |

FOREIGN PATENT DOCUMENTS

| | | |
|---|---|---|
| DE | 10014472 A1 | 10/2001 |
| FR | 2780744 A1 | 1/2000 |
| WO | WO-0035496 A1 | 6/2000 |
| WO | WO-2007107784 A2 | 9/2007 |

OTHER PUBLICATIONS

International Preliminary Report on Patentability, 2 pages, Dec. 17, 2009, PCT/US2008/006505.

Supplementary European Search Report, Mailed on Jun. 6, 2011, 8 pages, Application No. 087546180.0-2113/2155266, PCT/US2008006505.

Extended European Search Report Dated Jan. 11, 2012, Application No. 11192484.1 1-2113, 5 Pages.

Japanese Patent Office Action, Patent Application No. P2010511158, Jun. 5, 2012, 9 Pages.

Chinese Office Action Jun. 5, 2012, app No. 200880018910.5, 35 Pages.

Australian Patent Examination Report No. 1, 3 Pages, Patent Application—2008262456, Jul. 3, 2012.

European Patent Office Action, EP11192484.1, 2 Pages, Nov. 2, 2012.

\* cited by examiner

DEVICE TO PROMOTE HAND SANITIZATION

CROSS REFERENCE TO RELATED APPLICATIONS

This application is a continuation of application Ser. No. 12/070,429, filed on Feb. 19, 2008, which claims the benefit of U.S. Provisional Application No. 60/933,118, filed on Jun. 5, 2007, both of which are herein incorporated by reference.

BACKGROUND OF THE DISCLOSURE

1. Field of the Invention

Embodiments of the present invention generally relate to the prevention of disease transmission through proper hand sanitization and, more specifically, to a device to promote hand sanitization.

2. Description of the Related Art

Nosocomial, or hospital-acquired infections are a leading cause of death worldwide: in the US alone, they are responsible for 90,000 deaths annually. It has been shown that many nosocomial infections are contracted through contact with medical staff who have not properly sanitized their hands. Hospitals suggest that staff members sanitize their hands before every patient they contact. Thoroughly washing and scrubbing with water and antiseptic soap is the traditional method of hand sanitization in the hospital, but the time required for proper hand washing is unfeasible in a clinical setting because of the large numbers of patients that require care.

Repeated hand washing also causes dermatitis, which makes hands a better vector for bacterial transmission. Antiseptic gels and foams provide an alternative method of hand sanitization that is as effective as washing with soap and requires significantly less time. The widespread use of these antiseptics in hospitals has not resulted in decreased rates of nosocomial infections because healthcare staff still fail to comply with hand sanitization protocols. Although intentional non-compliance is one factor that lowers rates of compliance, it is likely that simply forgetting to sanitize between patients is the main culprit. It is well accepted that if health care workers improve compliance with hand-washing protocols, the incidence of nosocomial infections decreases substantially.

Therefore, there is a need in the art for a device that promotes hand sanitization.

SUMMARY

Embodiments of the present invention relate to a device to promote hand sanitization. In one embodiment of the present invention, the device comprises an assembly used to move a door coupled to a sanitizing agent dispenser such that the dispenser releases sanitizing agent upon manipulation of the assembly to move the door. In another embodiment, the assembly comprises a latch that is coupled to the door for latching the door. Upon manipulation of the latching assembly to open the door, hand sanitizing agent is automatically released from the latching assembly onto the hands of a user that is manipulating the latching assembly.

BRIEF DESCRIPTION OF THE DRAWINGS

So that the manner in which the above recited features of the present invention are attained and can be understood in detail, a more particular description of the invention, briefly summarized above, may be had by reference to the embodiments thereof which are illustrated in the appended drawings.

DETAILED DESCRIPTION OF THE DRAWINGS

Figure 1:
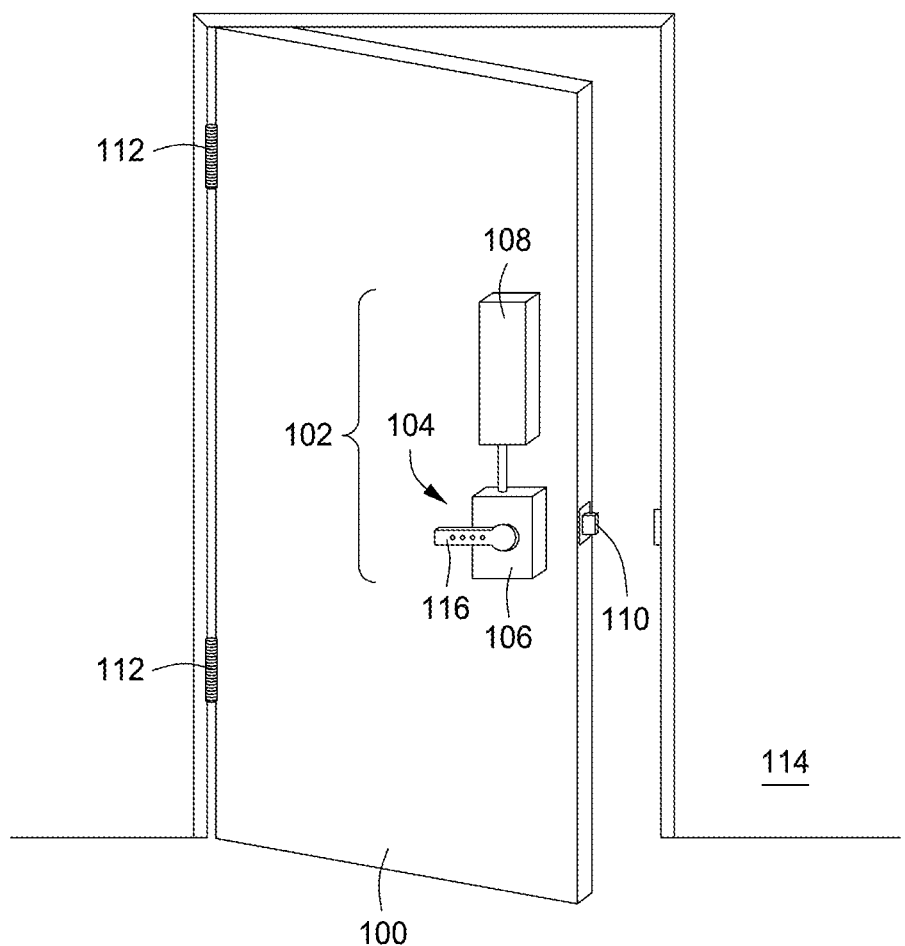
FIG. 1 depicts a perspective view of a hand sanitizing device coupled to a door in accordance with one embodiment of the invention.

FIG. 1 depicts a perspective view of a door 100 mounted by hinges 112 to a wall 114 of a room (or enclosure). In accordance with one embodiment of the invention, the door 100 comprises a device 102 to promote hand sanitization. The device 102 comprises an assembly 104 coupled to a sanitizing agent dispenser 106. The assembly 110 comprises a handle 116 and, in some embodiments, a latch 110 that can be manipulated to open and close the door 100 with respect to the wall 114. The sanitizing agent dispenser 104 comprises, or is coupled to, a reservoir 108 containing a liquid or gel sanitizing agent. The sanitizing agent is dispensed via the handle 116 of the assembly, such that manipulation of the assembly to open or close the door 100 results in the sanitizing agent being dispensed upon a user's hand.

Figure 2:
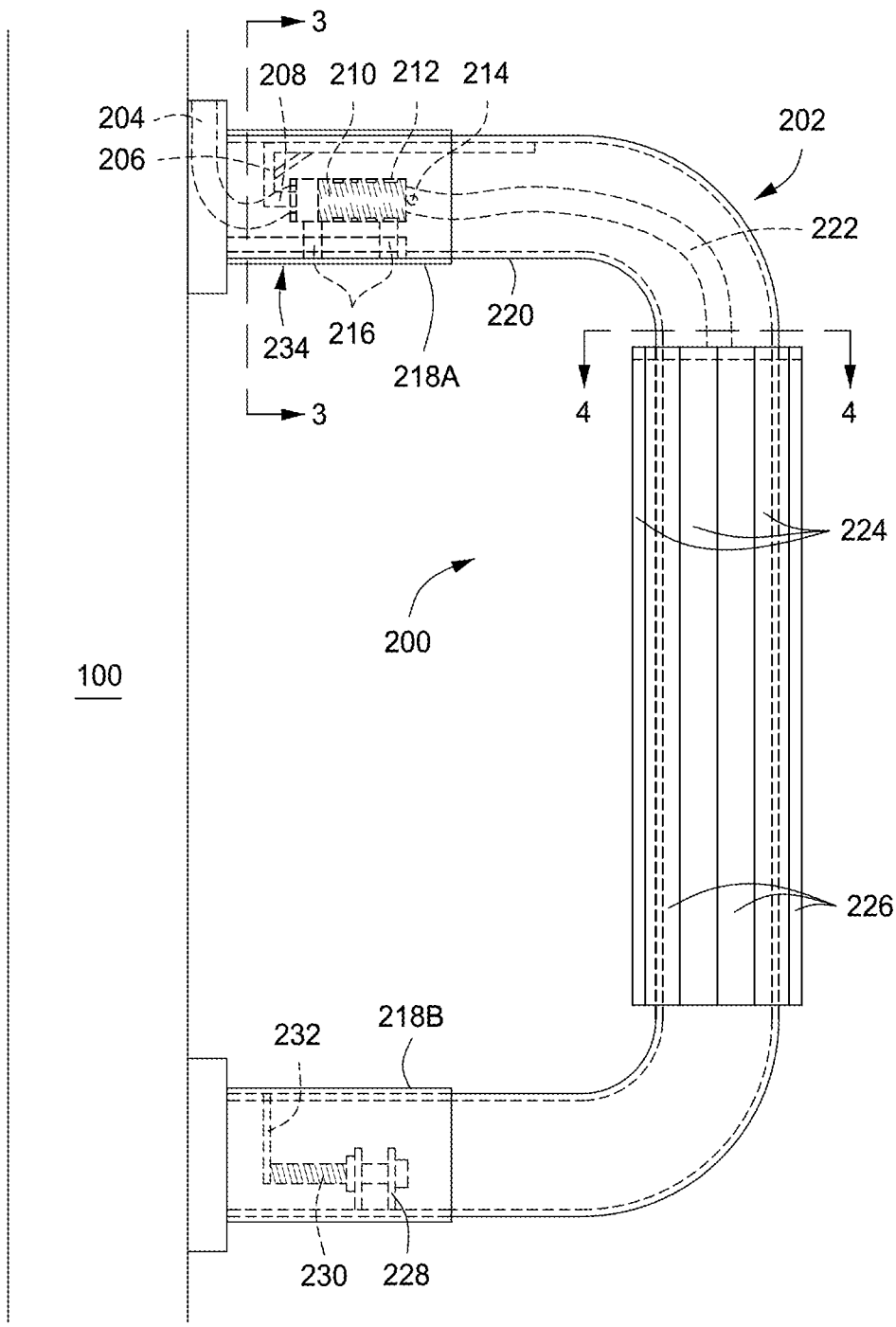
FIG. 2 depicts a perspective view of a pull handle in accordance with one embodiment of the present invention.

FIG. 2 depicts a perspective view of a pull handle 200 (a form of assembly used to move a door that may or may not manipulate a latch for the door) mounted to a door 100 where the pull handle 200 includes sanitizing agent dispenser 202 in accordance with another embodiment of the invention. The handle 200 comprises a hollow C-shaped tube 220 that is moveably coupled to a pair of handle sleeves 218A and 218B that are affixed to the door 100. The dispenser 202 comprises a pump 234, a tube 204 from a sanitizing agent reservoir (not shown), a distribution tube 222, agent supply channels 226 and a permeable foam grip 224. The pump 234 is mounted on a pair of pump stanchions to the handle sleeve 218A. The pump 234 comprises a pump piston 208, a pump spring 212, and a ball valve 214 that are organized to pump fluid from tube 204 into tube 222. The tube 222 couples the fluid to the channels 226 as discussed below with respect to FIG. 4. The sanitizing agent penetrates the grip material 224 to contact a hand that manipulates the handle 220. An alternative to a permeable grip is a handle surface comprising perforations.

Within the handle 220 proximate the handle sleeve 218B is a spring support 232, a spring 230, and a spring plate 228. Together these elements form a biasing assembly that maintains the handle inward position such that pulling the handle applies force against the bias, causes the pump to pump sanitizing agent and then returns the handle to the inward position. In this manner, upon each pull of the handle, an amount of sanitizing fluid is pumped out of the handle onto a user's hand.

Figure 3:
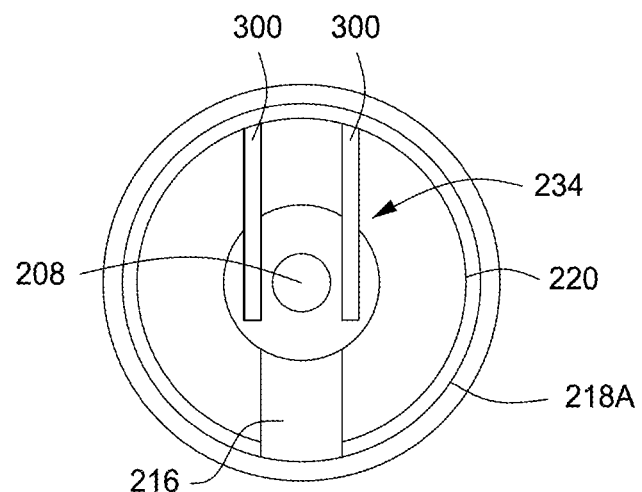
FIG. 3 depicts a cross section plan view of a pump within the embodiment of FIG. 2.

FIG. 3 depicts a cross sectional view of pull handle 200 along line 3-3 in FIG. 2 showing the pump 234 mounted by a stanchion 216 to the sleeve 218a. An actuator 300 is coupled to the handle 220 such that movement of the handle 220 relative to the sleeve 218A causes the piston 208 of the pump 300 to force sanitizing agent toward the grip. In this manner, the pump 234 is embedded within the handle in an unobtrusive manner.

Figure 4:
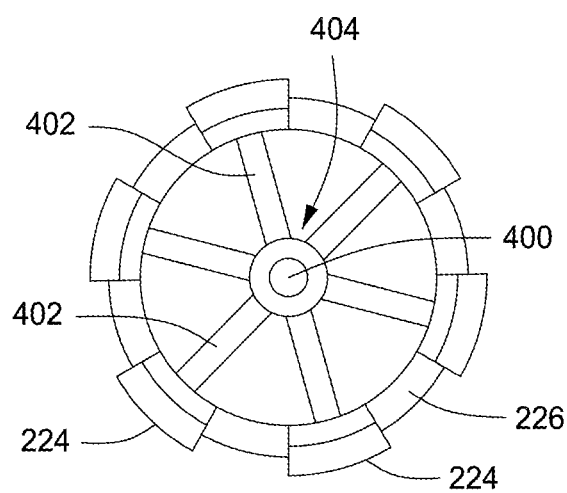
FIG. 4 depicts a cross section plan view of the pull handle of FIG. 2.

FIG. 4 depicts a cross sectional view of the pull handle 200 along line 4-4 of FIG. 2. A plenum 404 for distributing sanitizing agent to the handle grip 224 is formed of a central tube 400, a plurality of radial tubes 402 and channels 226. As the sanitizing agent is pumped into the central tube 400 (coupled to tube 222 of FIG. 2), the agent flows equally into the "spokes" 402, through the channels 226 and the permeable grip 224.

Figure 5:
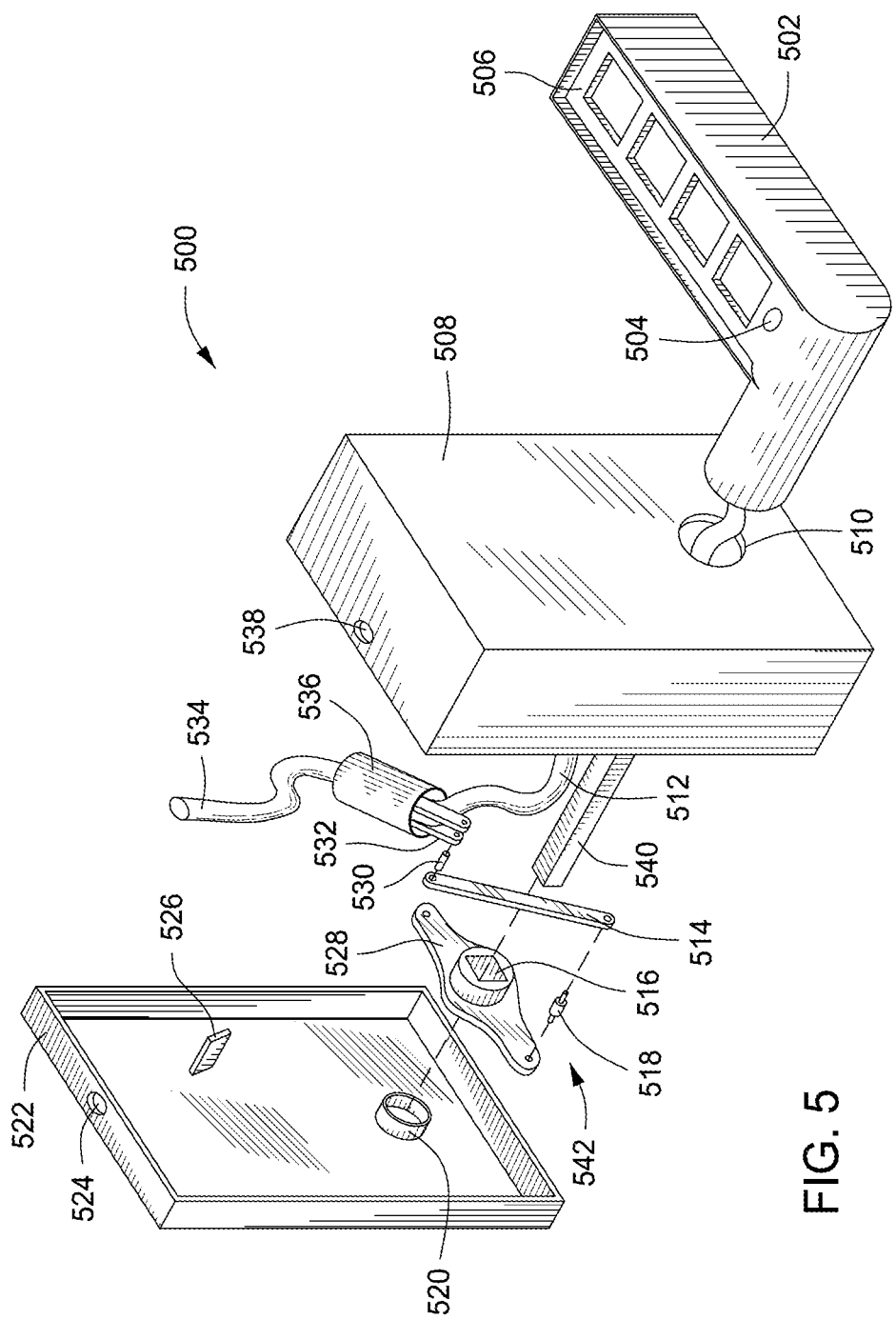
FIG. 5 depicts an exploded view of a twist latch handle in accordance with another embodiment of the invention.

FIG. 5 depicts an exploded view of an assembly 500 that utilizes a twist handle 502 to facilitate pumping sanitizing agent in accordance with another embodiment of the invention. The assembly 500 comprises a mounting plate 522, housing 508, and a handle 502. Within the housing 508 is a pump 536 and a pump actuator 542. The pump actuator 542 couples the handle 502 to the pump 536. The pump 536 receives sanitizing agent via a tube 534. An outlet of the pump 536 is coupled to the tube 512 and, ultimately, to the handle 502. The inlet tube 534 is threaded through a hole 524 in the mounting plate 522 to couple to a sanitizing agent reservoir (not shown).

The actuator 542 comprises a cam 528 and a push rod 508. The cam 528 is coupled to a pair of pump arms 532 via the push rod 514. The push rod 514 is coupled, at its first end, to the arms 532 using a pin 530. At its second end, the push rod 514 is coupled to the cam via a pin/spacer 518. The cam 528 comprises a centrally located aperture 516 that interacts with a latch shaft 540. The latch shaft 540 (typically, having a square cross section) passes through a matching shaped aperture 516. The shaft 540 exits the mounting plate through a hole 520 to engage a portion of a conventional latch assembly (not shown). The shaft 540 couples to the handle 502 via a hole 510 in the housing. In addition, the tube 512 passes through the hole 510.

The tube 512 supplies sanitizing agent to an agent port 504. The agent flows into a tray 506 atop the handle 502 such that a user must contact the agent to twist the handle 502. Alternatively, the handle may comprise a plenum and distribution channels to position the agent on the handle 502. A permeable grip, as described previously, may also be positioned upon the handle 502, such an embodiment is described with respect to FIG. 6 below.

In operation, a twisting motion of the handle 502 to facilitate unlatching a door causes the pump 536 to distribute sanitizing agent to the tray 506 of the handle 502. Consequently, the user receives sanitizing agent upon their hand.

Figure 6:
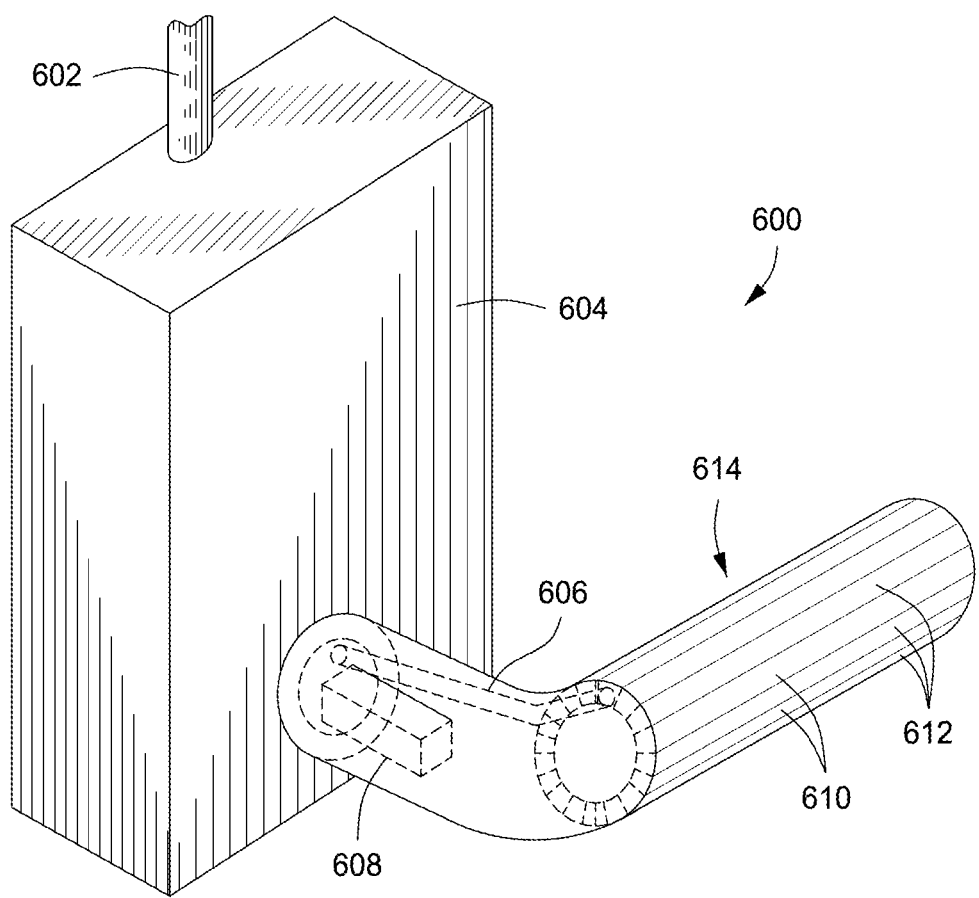
FIG. 6 depicts a perspective view of another embodiment of a twist latch handle in accordance with another embodiment of the invention.

FIG. 6 depicts a perspective view of another embodiment of the invention that utilizes a twist handle 614 to facilitate pumping of sanitizing agent. A source tube 602 couples sanitizing agent from a reservoir (not shown) to the pump (the same assembly as shown in FIG. 5) located within the housing 604. The shaft 608 is coupled to the handle 614 to facilitate coupling the rotation of the handle to the pump as well as other portions of the actuator assembly. The tube 606 carrying sanitizing agent from the pump is coupled to the grip 610 of the handle 614. The handle 614 is covered with a permeable foam 612 such that the sanitizing agent permeates the foam. With each grasp of the handle 614, a user will receive sanitizing agent upon their hand. Other forms of sanitizing agent distribution are also within the scope of the invention such as a plenum and a perforated handle surface and the like.

Figure 7:
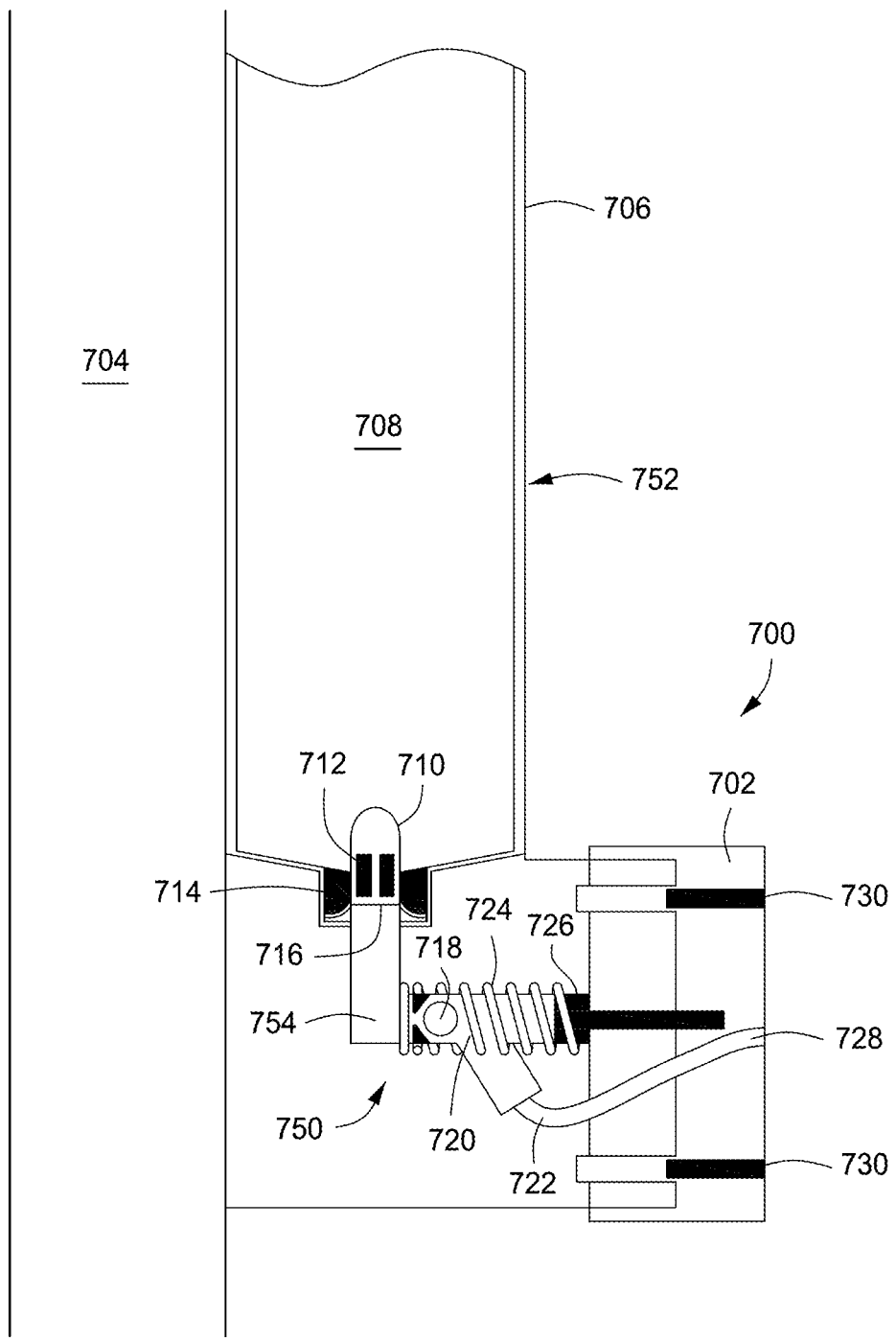
FIG. 7 depicts a cut away view of push latch assembly in accordance with another embodiment of the present invention.

FIG. 7 depicts a cross sectional view of another form of assembly 700 wherein a latch may be actuated by a push panel or push bar 702 and the sanitizing agent dispenser 750 is incorporated into the assembly 700 to dispense agent upon depression of the push bar 702. Coupling the push bar to a door latch forms an alternative embodiment of the invention. The dispenser 750 comprises a sanitizing agent reservoir 752 and a pump 720. The reservoir 752 comprises a casing 706 and a replaceable cartridge 708 (further described with respect to FIG. 10, below). The cartridge 708 is coupled to the pump via a cannula 710 that extends through a cap 714 into the cartridge 708. Upon installation of the cartridge 708, the cannula 710 pierces a septum 716 to position the apertures 712 into the agent. The apertures 712 couple agent to the tube 754, which carries the agent to the pump 720. The pump 718 comprises a ball valve 718, a spring 724, and a piston 726. The piston 726 is coupled to the bar 702 such that depression of the bar 702 causes the pump to push fluid through the tube 722 to the outlet 728 at the surface of the bar, or button 702. The bar is guided in its motion by guide pins 730.

In operation, a user depresses the bar or button 702 and the pump is actuated to supply a stream of sanitizing agent to the outlet 728. The agent is applied to the person's hand that pushes the bar or button to move a door. The actuator for the door may be remote, as in a handicapped door opener, or may be local and built into a portion of the bar proximate the dispenser 750.

Figure 8:
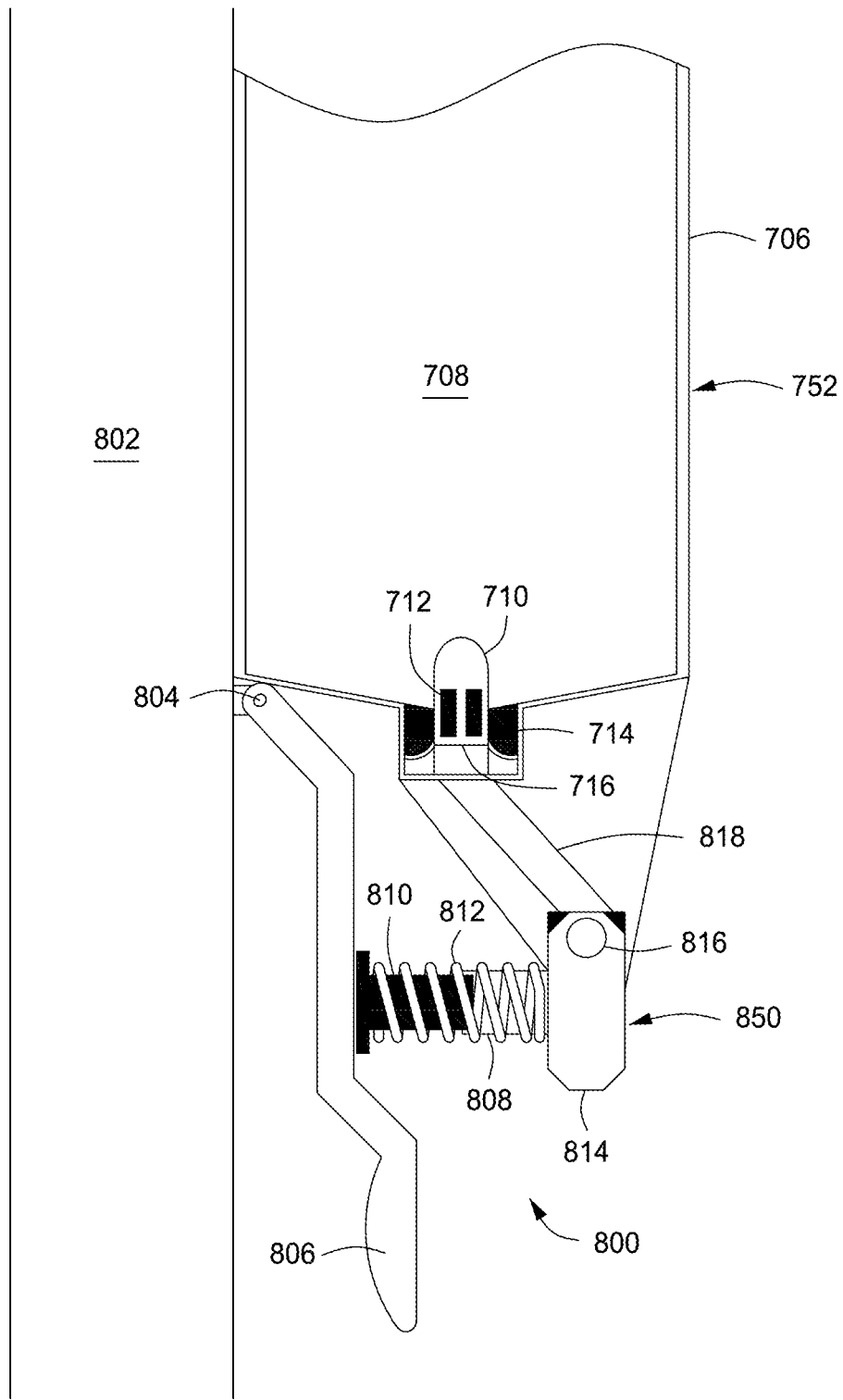
FIG. 8 depicts a cut away view of a pull handle in accordance with another embodiment of the present invention.

FIG. 8 depicts a cross sectional view of another form of assembly 800 wherein a latch may be actuated by a pull panel 806 and the sanitizing agent dispenser 850 is incorporated into the assembly 800 to dispense agent upon pulling of the pull panel 806. Coupling the assembly 800 to a latch forms an alternative embodiment of the invention. The dispenser 850 comprises a sanitizing agent reservoir 752 and a pump 808. The reservoir 752 is substantially similar to the reservoir 752 described above and further described with respect to FIG. 10, below. Once installed, the apertures 712 couple agent to the tube 818, which carries the agent to the pump 808. The pump 808 comprises a ball valve 816, a spring 812, and a piston 810. The piston 810 is coupled to the panel 806 such that pulling of the panel 806 causes the pump 808 to push fluid through an outlet nozzle 814 located proximate the pull panel 806. The pull panel is guided in its motion by a pivot 804.

In operation, a user pulls the panel 806 and the pump 808 is actuated to supply a stream of sanitizing agent to the outlet nozzle 814. The agent is applied to the person's hand that pulls the panel to move a door. The actuator for the door may be remote, as in a handicapped door opener, or may be local and built into a portion of the panel proximate the dispenser 850.

Figure 9:
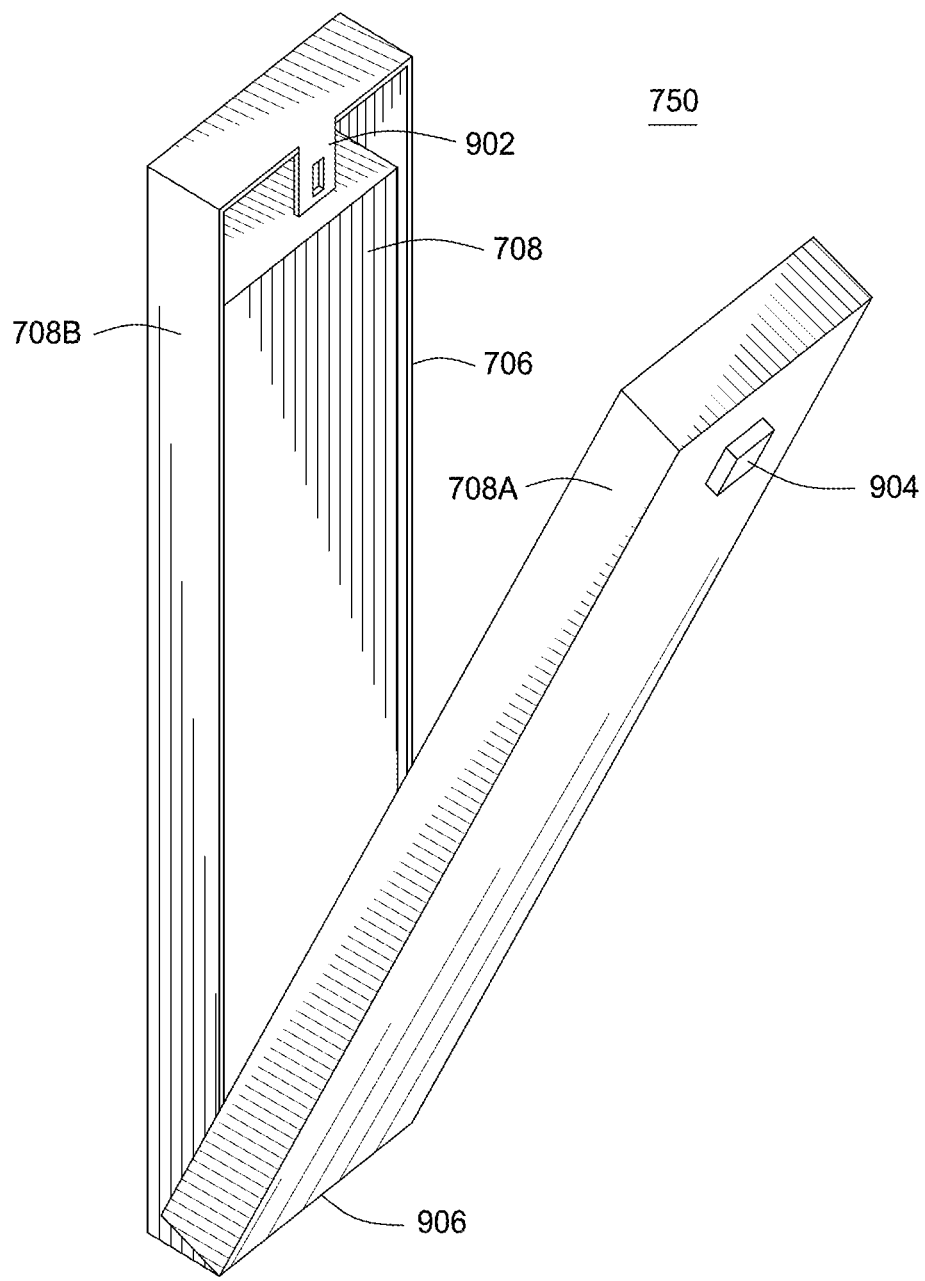
FIG. 9 depicts a perspective view of a cartridge casing in accordance with an embodiment of the invention.

FIG. 9 depicts a perspective view of one embodiment of a reservoir 750. The reservoir comprises a casing 708 and a cartridge 706 that contains the sanitizing agent. The casing comprises a latch 902 and a latch release button 904 as well as a hinge 906. Upon depressing the latch release button 904, the latch is released to enable pivoting an outer casing 708A away from the inner casing 708B to facilitate access to the cartridge 706. In this manner, a cartridge 706 can be readily replaced. The casing may have a viewing port to enable checking whether the sanitizing agent cartridge is empty. Although the hinge and latch are shown at the top and bottom of the casing, in other embodiments the casing may be hinged along the top or side and a latch may or may not be used.

Figure 10:
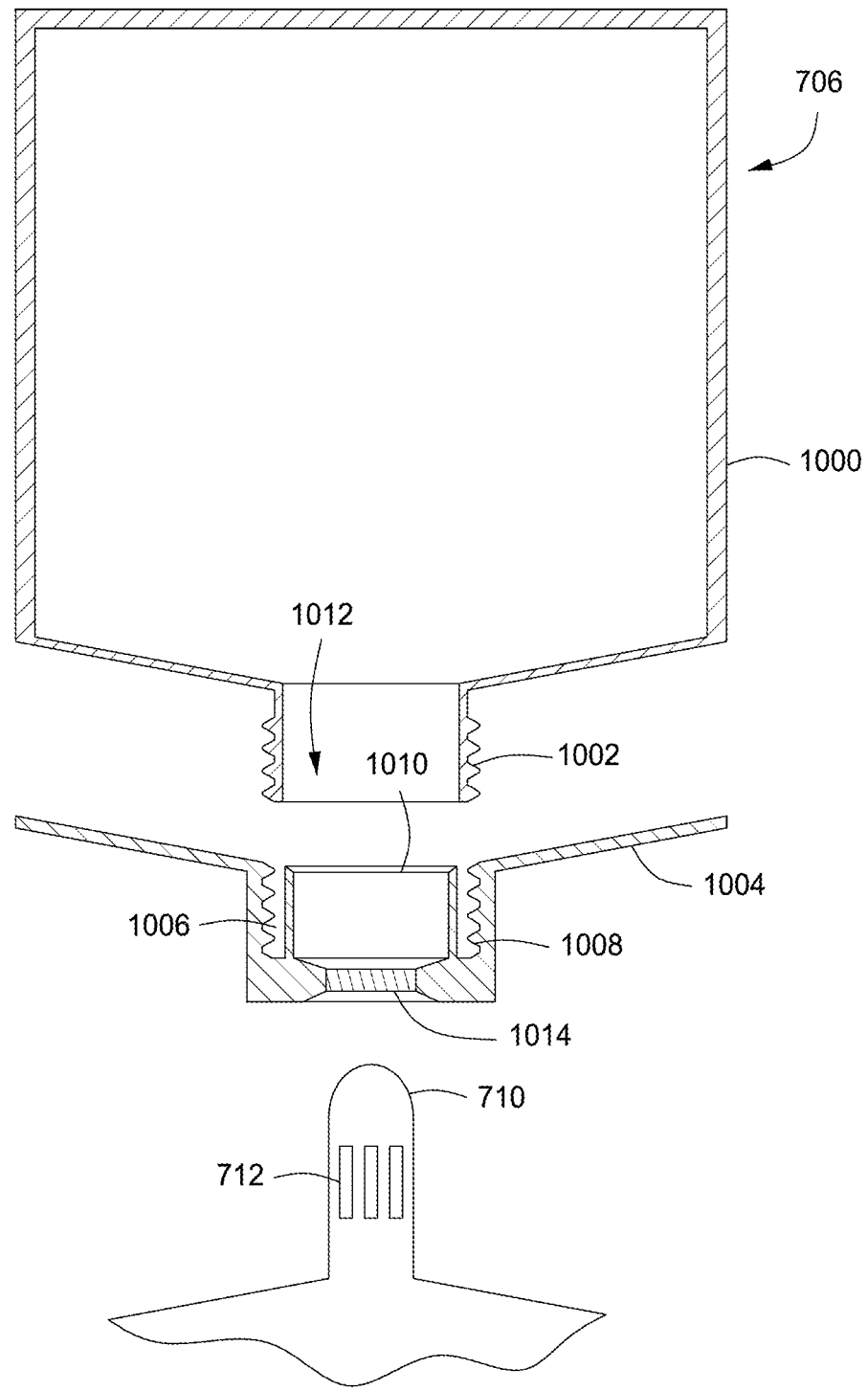
FIG. 10 depicts a cross-sectional view of a cartridge for storing sanitizing agent in accordance with an embodiment of the invention.

FIG. 10 depicts a cartridge 706 for providing a source of sanitizing agent to the device to promote sanitization as described above. The cartridge 706 comprises a container 1000 and a cap 1004. The container 1000 is a bottle or bag capable of containing a liquid or gel. The container has an opening 1012 that is surrounded by threads 1002. The cap comprises a threaded annular slot, where the threads interface with the threads of the container 1000. The cap 1004 further comprises a rubber septum 1014 and a seal 1010. The seal 1010 ensures that the sanitizing agent is maintained in sterile environment. The seal also retains the agent when the cartridge has the opening facing downward. The seal 1010 is irreversibly penetrated and opened by the cannula when the cartridge 706 is installed in the casing (see FIG. 9).

Although the foregoing description used a door to a room as an example of an object that the device to promote hand sanitization can be incorporated, those skilled in the art will realize that other doors and moveable objects can be benefited by incorporation of the invention. For example, desk drawers, file drawers, cabinet doors or drawers or any other object that is repeatedly touched and moved by various persons can utilize the device to promote hand sanitization. Generally speaking, the device can be incorporated into any form of handle for a door or other object. Such devices may or may not include latching assemblies.

While the foregoing is directed to the illustrated embodiments of the present invention, other and further embodiments of the invention may be devised without departing from the basic scope thereof, and the scope thereof is determined by the claims that follow.

What is claimed is:

1. A device for promoting hand sanitization, the device comprising:
   an assembly used to move a door, the assembly comprising:
   a pull handle having perforations on a surface;
   a pump coupled to the pull handle; and
   a sanitizing agent dispenser, coupled to the assembly, wherein, upon manipulation of the assembly to move the door, a sanitizing agent is simultaneously released though the perforations on the surface of the pull handle onto a hand of a user, wherein the assembly comprises a spring support affixed to the pull handle, a spring, and a spring plate coupled to the pull handle, the spring biasing the pull handle in an inward position and wherein pulling the pull handle outward applies force against the biasing and causes the pump to pump the sanitizing agent, the biasing returning the pull handle to the inward position upon release of the pull handle.

2. The device of claim 1 wherein the pump comprises a piston, a pump spring, and a ball valve.

3. The device of claim 2 wherein the assembly comprises at least one handle sleeve.

4. The device of claim 1 wherein the pull handle further comprises a central tube, a plurality of radial tubes, and a plurality of channels, where the sanitizing agent is delivered from the central tube through the radial tubes to the plurality of channels.

5. The device of claim 4 wherein the plurality of channels are covered by a permeable foam.

6. The device of claim 1 wherein the assembly is adapted to manipulate a latch of the door.

7. The device of claim 1 wherein the sanitizing agent dispenser comprises a reservoir containing the sanitizing agent.

8. The device of claim 7 wherein the reservoir comprises a casing and a cartridge.

9. The device of claim 8 wherein the cartridge comprises a cap having a rubber septum and a seal.

10. The device of claim 9 wherein the sanitizing agent dispenser comprises a cannula that pierces the seal upon installation of the cartridge within the casing.

11. The device of claim 1 wherein the device is coupled to at least one desk drawers, file drawers, cabinet doors or drawers on any other object that is repeatedly touched and moved, promoting hand sanitization of the user.

12. The device of claim 1 wherein the device can be incorporated into the handle for a door or drawers and is coupled to latching assemblies.

13. The device of claim 1 wherein the assembly further comprises a pull panel coupled to a pivot.

14. An apparatus for dispensing a sanitizing agent onto at least one hand of a user comprising:
   a door;
   a latching assembly, coupled to the door, comprising a C-shaped pull handle having perforations; and
   a sanitizing agent dispenser, coupled to the latching assembly and the C-shaped pull handle for dispensing the sanitizing agent through the perforations of the C-shaped pull handle simultaneously onto the at least one hand of the user when the pull handle is pulled and the latching assembly is manipulated to open the door, wherein the latching assembly including a biasing means comprising a spring support affixed to the pull handle, a spring, and a spring plate coupled to the pull handle, the spring biasing the pull handle in an inward position and wherein pulling the pull handle outward applies force against the biasing and causes the dispenser to dispense the sanitizing agent, the biasing returning the pull handle to the inward position upon release of the pull handle.

* * * * *